United States Patent
Kishigami

[11] Patent Number: 5,458,577
[45] Date of Patent: Oct. 17, 1995

[54] COMPOSITE SYRINGE

[75] Inventor: Yoshikazu Kishigami, Otu, Japan

[73] Assignee: Nissho Corporation, Osaka, Japan

[21] Appl. No.: 264,342

[22] Filed: Jun. 23, 1994

[30] Foreign Application Priority Data

Jul. 23, 1993 [JP] Japan .......... 202723

[51] Int. Cl.⁶ .......... A61M 5/32
[52] U.S. Cl. .......... 604/192; 604/198; 604/263
[58] Field of Search .......... 604/110, 192, 604/198, 263, 187, 111

[56] References Cited

U.S. PATENT DOCUMENTS

| | | | |
|---|---|---|---|
| 4,300,678 | 11/1981 | Gyure et al. | 206/364 |
| 4,631,057 | 12/1986 | Mitchell | 604/198 |
| 4,997,422 | 3/1991 | Chow et al. | 604/198 |
| 5,324,264 | 6/1994 | Whitaker | 604/111 |
| 5,336,186 | 8/1994 | Haber et al. | 604/110 |
| 5,342,309 | 8/1994 | Hausser | 604/110 |
| 5,376,080 | 12/1994 | Petrussa | 604/198 |

FOREIGN PATENT DOCUMENTS

| | | |
|---|---|---|
| 0288879A2 | 11/1988 | European Pat. Off. . |
| WO89/10150 | 11/1989 | WIPO . |
| WO92/06725 | 4/1992 | WIPO . |
| WO93/02728 | 2/1993 | WIPO . |

*Primary Examiner*—John D. Yasko
*Attorney, Agent, or Firm*—Ronald J. Kubovcik

[57] ABSTRACT

A composite syringe has an injector body and a cylindrical protector which covers a cylinder of the injector body. The protector includes a sleeve separably connected to a base which is secured to an outer periphery of the cylinder's forward end. The sleeve, when separated from the base, is caused to slide towards the cylinder's end and beyond a tip holding a needle, until it engages again with the base at a position where the needle is covered entirely with the sleeve. This prevents any accident of erroneous pricking or puncture of a user of the syringe or other people coming into contact with the syringe.

10 Claims, 3 Drawing Sheets

COMPOSITE SYRINGE

BACKGROUND OF THE INVENTION

1. Field of the Invention

The present invention relates to a disposable composite syringe, and, more particularly, relates to a composite syringe in which the needle can be sealed so as to prevent erroneously pricking or puncturing people who may come into contact with the syringe.

2. Description of the Prior Art

Every medical needle, once used, is usually thrown away, whether it is an ordinary needle of the injector type or a vein needle retained for intravenous drip injection of a liquid medicine or for transfusion of blood. The acute needle ends are covered with proper protectors, before being discarded, in order to prevent injury to the people who come into contact with the needles. However, those who work in various medical fields and handle the needles are still exposed to danger, because the needle ends may possibly cause injury when attaching the protectors thereto. Such an accident could cause a serious problem in addition to the simple pain due to a skin prick. For example, the needle ends which have been used on patients are sometimes polluted or exposed to various pathogens such as bacilli and viruses, thereby exposing healthy people to such bacilli and viruses.

Many ideas directed to prevention of such an erroneous exposure by the used needles include those which are disclosed in the Japanese Unexamined Utility Model Publications: Sho. 60-55448; Sho. 61-85239; Hei. 4-58256, the Unexamined Patent Publications: Hei. 4-244167; Hei. 2-1288; Hei. 4-90766; Sho. 62-144666; Sho. 63-317160; Sho. 64-86981, and the Domestic Re-Publication of Unexamined International Patent Application: Hei. 3-504808.

Publications 60-55448 and 61-85239 disclose protectors that have sockets of a modified shape. An example of the sockets has an enlarged diameter enlarged towards its end with another socket having a flange adjacent thereto, and still another socket has slits extending longitudinally thereof.

Disclosed in Publications 4-58256 and 4-244167 are some specially designed protectors. One of them has a bellows that can be stretched towards an end thereof to fully cover the injector. The other protector comprises a housing that consists of a basal portion and a compressible portion flexibly connected thereto. An acute end of the injector needle accommodated in this housing is caused to pierce the retracted compressible portion.

Disclosed in Re-Publication 3-504808, Publications 2-1288 and 4-90766 are injectors each comprising a retractable needle. Plungers engage with and retract the used needles into outer cylinders.

Further, Publications 62-144666, 63-317160 and 64-86981 disclose injectors each having a cylindrical protector fitted on an outer cylinder. This protector is slidable longitudinally of the cylinder so as to cover the whole injector.

The various prior art injectors listed and discussed above seem to be effective in preventing the needles from unintentionally pricking the user's skin. However, they still are disadvantageous for the following reasons.

The modified socket protectors must be removed from and fitted again on the used injectors. Such a re-fitting of the socket will possibly cause an accidental, erroneous pricking of the skin. Sockets of a complicated structure will increase manufacturing cost and complicate use of the injectors.

Injectors having retractable needles cannot be manufactured merely by modifying the conventional design of ordinary injectors. A sophisticated structure for injectors of this type will not only render them expensive but also difficult to use.

Injectors of the other type having the slidable protectors are easier to operate, although certain means or members for slidably holding the protectors must be added to the ordinary injectors. Such additional means or members will also increase manufacture cost.

SUMMARY OF THE INVENTION

As a solution to the foregoing problems, it is an object of the present invention to provide an improved composite syringe that is simpler in structure, easier to operate and less expensive.

In order to achieve this object, a composite syringe provided herein comprises an injector body in combination with a cylindrical protector. The injector body comprises a cylinder, a tip extending therefrom to hold a medical needle, and a skirt extending coaxially with the tip so as to surround the tip. The protector is composed of a sleeve and a base, extending forwards therefrom, to grasp or encircle the tip. The sleeve has its forward end breakable from a rear end of the base, so that the sleeve can be broken off or detached from the base and slide forward on and along the cylinder. The composite syringe further has a lockable member formed on an inner periphery of the sleeve, and a locking member formed on an outer periphery of the base. The locking member is engageable with the lockable member so that the sleeve can be kept at a position to cover the whole needle.

The base and the separable sleeve may be connected one to another by one or more thin bridges. Alternatively, the base may be integral with the sleeve provided that they are made of materials that are substantially immiscible with each other.

The lockable member may preferably be lugs disposed on a rear end portion of the sleeve and engageable with an annular groove formed as the locking member on the base. Contrarily, the lockable member may be an annular groove engageable with lugs formed as the locking member.

After use of the composite syringe, the protector's sleeve will be gripped by one hand, with a flange of the cylinder being twisted relative to the sleeve by the other hand. Then, the sleeve thus separated from the base and rendered longitudinally displaceable of the syringe will be moved forwards, so that the locking member moves into engagement with the lockable member at its position where the sleeve covers the whole needle for safe disposal of the used syringe.

BRIEF DESCRIPTION OF THE DRAWINGS

Now, embodiments of the present invention will be described referring to the drawings, in which.

DETAILED DESCRIPTION OF THE PREFERRED EMBODIMENTS

Figure 1:
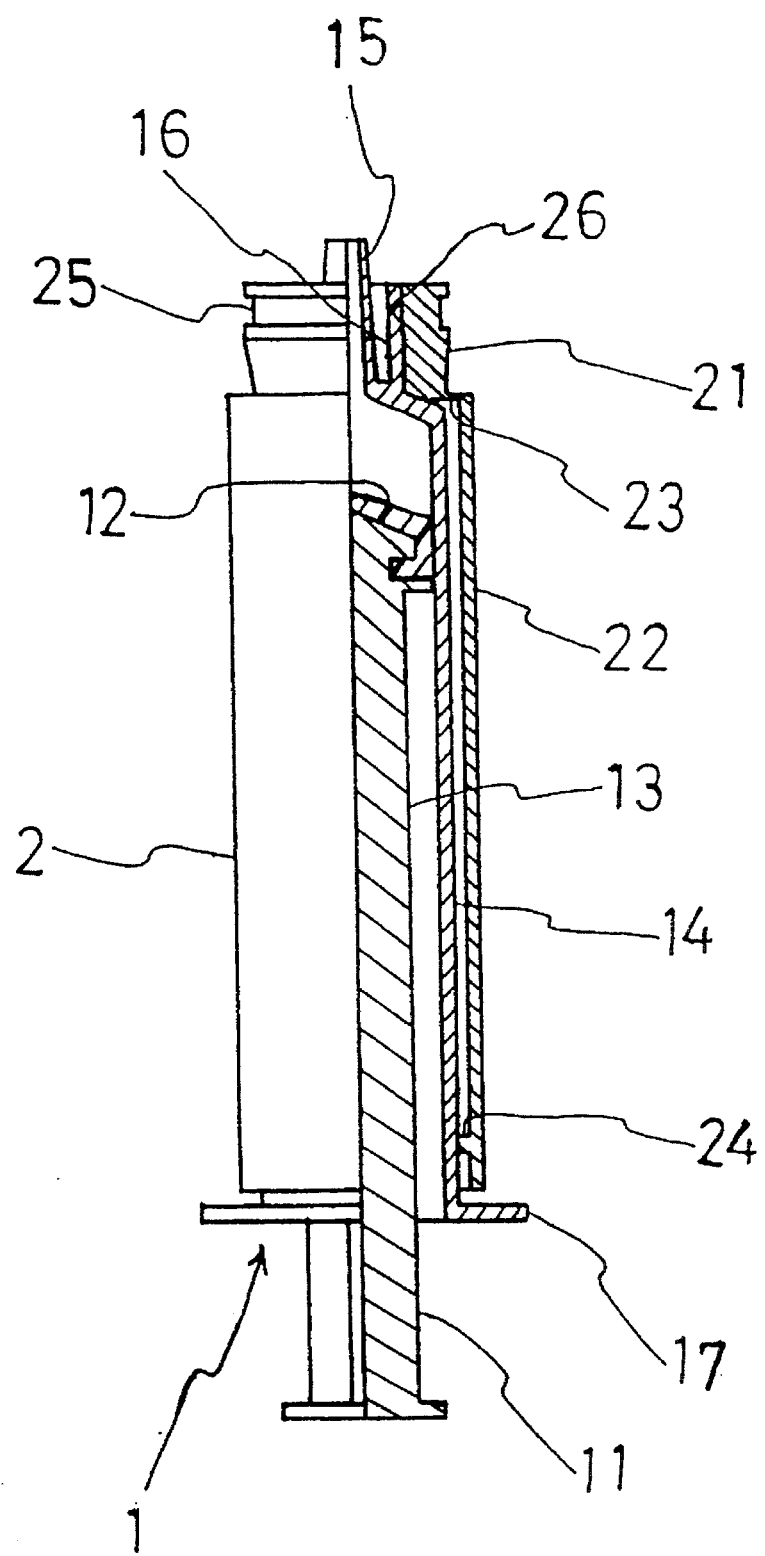
FIG. 1 is a plan view of a composite syringe comprising a protector in an embodiment, with a longitudinal half of the protector being shown in cross section.
Figure 2:
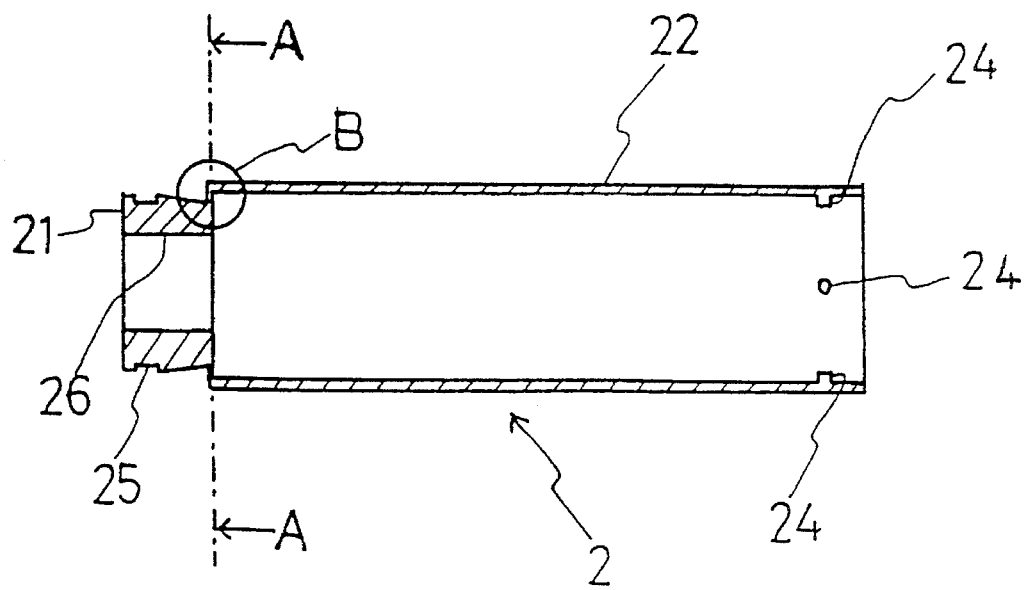
FIG. 2 is a cross-sectional view of the protector, taken along an axis thereof.
Figure 3:
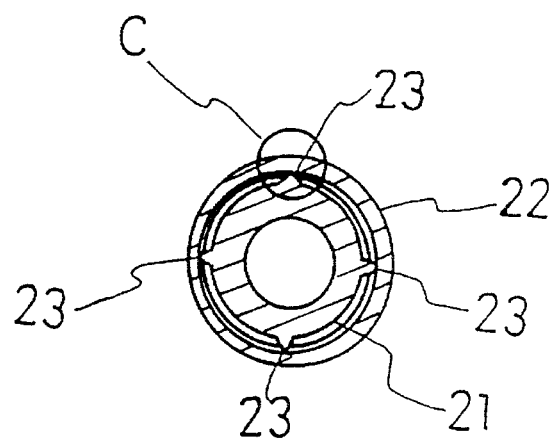
FIG. 3 is a cross section taken along the line A—A in FIG. 2.
Figure 4:
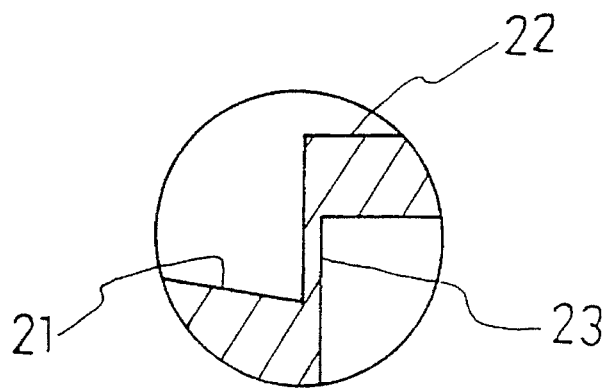
FIG. 4 shows an encircled portion B in FIG. 2, on an enlarged scale.
Figure 5:
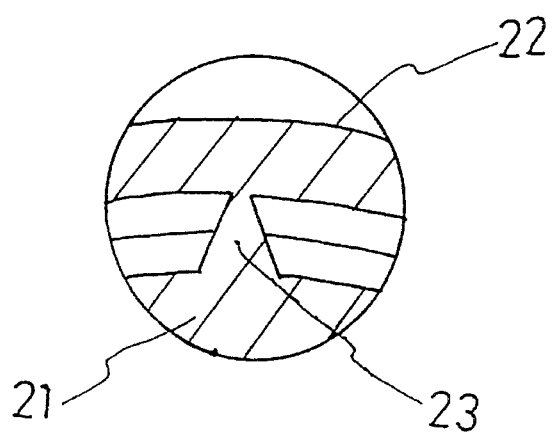
FIG. 5 shows an encircled portion C in FIG. 3, on an enlarged scale.

FIG. 1 illustrates a composite syringe provided in an embodiment of the present invention. The syringe comprises an injector body 1 and a cylindrical protector 2 fitted on a cylinder 14 of the injector body. The protector 2 comprises a base 21 and a sleeve 22, with the base 21 secured to an outer periphery of a forward end of the cylinder 14. The sleeve 22 connected to the base 21 is separable therefrom and, if so separated, can slide towards a forward end of the cylinder 14 to a position where a needle 3 held by a tip 15 is wholly covered. The sleeve will immovably engage again with the base 21 at that forward end position.

The injector body 1 comprises a skirt 16, in addition to a tip 15 for holding a needle as in the case with ordinary injectors. The skirt 16 employed in the present invention surrounds and extends coaxially of the tip 15. Typically, the ordinary injectors are of the so-called "lockable" type in which the needles are screwed to or "Luer-connected" to the tips. Thus, the injector body 1 can be of any conventional type, and no detailed description thereof will be given here. As FIG. 1 shows, a plunger 11 inserted in the cylinder 14 of this body 1 comprises a rod 13 and a gasket 12 secured to a forward end of the rod. A flange 17 formed integral with a rear end of the cylinder 14 will bear against the first and second fingers of a user when he or she presses the plunger 11 in a forward direction with his or her thumb. The tip 15 is formed at the forward end of the cylinder 14, as noted above, and is surrounded by the skirt 16 which extends coaxially of the tip. The needle 3 may be screwed to an inner peripheral thread (not shown) of the skirt, or alternatively be locked therein by the "Luer" connection.

The protector 2, comprising the base 21 and the sleeve 22, is of a cylindrical shape to cover the cylinder 14 of the injector body 1. The base 21 has an inner periphery 26 firmly held in place on an outer periphery of the forward end, i.e., skirt 16. The sleeve 22 extends rearward from a rearward end of the base 21 and terminates a little short of the flange 17 of the cylinder 14. The rearward end of the base 21, connected to a forward end of the sleeve 22, is readily separable from the sleeve 22, for example, by twisting the sleeve relative to the base. The sleeve 22, if separated from the base, can slide forwards on and along the cylinder 14 of the injector body 1. Thus, the sleeve 22 can be moved to a position so as to wholly cover the needle held by the tip 15. An annular groove 25 is formed as the locking member around a forward portion of the base 21. The base 21 is tapered to increase its diameter from its rearward end in a direction towards the groove. Lugs 24 protrude from an inner periphery of the rear end of the sleeve 22 and serve as a lockable member. These lugs 24 will engage with the annular groove 25 when the sleeve is moved to its foremost position so as to cover the needle in its entirety (see FIG. 7).

In the example of FIG. 1, thin bridges 23 connect the sleeve 22 to the base 21 of the protector in the manner shown in FIGS. 2 to 5. In other examples not shown, an intentional weld line, (i.e., an imperfectly welded zone) is formed along the boundary between the base and the sleeve, or two materials of different colors and immiscible with one another may form the base and sleeve, respectively. The number of thin bridges is preferably two or more, though a single bridge will suffice.

The lockable and locking members for keeping the sleeve at the aforesaid foremost position covering the needle need not necessarily be the lugs and groove, respectively, formed on or in the sleeve and the base. Instead, the sleeve may be formed with an inner, annular groove in which lugs, provided on the base, are received in the groove. The lockable and locking members may be of other shapes, and a single or annular lug may be used to lock the sleeve to the base.

Figure 6:
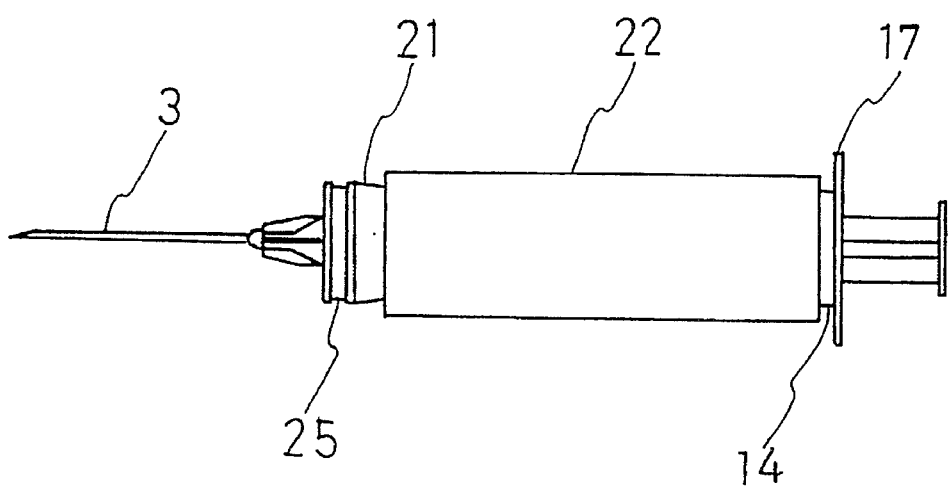
FIG. 6 is a plan view of the composite syringe shown in FIG. 1 with a needle attached thereto and having the protector.
Figure 7:
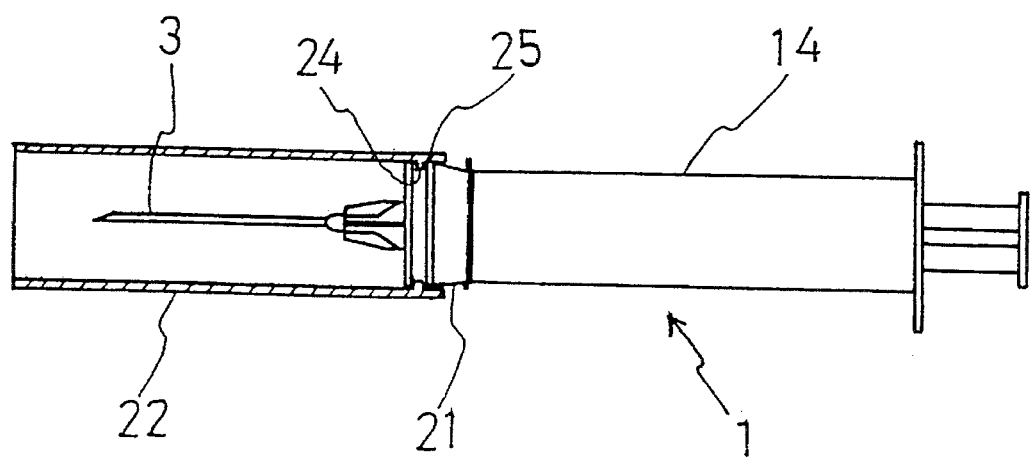
FIG. 7 is a plan view of the protector shown in FIG. 6 and comprising a sleeve and a base, with the sleeve (shown in cross section) shifted forwards to engage with the base.

FIGS. 6 and 7 illustrate operation of the composite syringe of the present invention.

As shown in FIG. 6, the needle 3, before use, is mounted on the tip 15 of the cylinder 14. The syringe 1 is used in medical operations such as the injection of a liquid medicine or the collection or transfusion of blood. After use in the medical operation, the composite syringe will be discarded in the following manner. An operator grips the sleeve 22 with one of his or her hands, and grips the flange 17 of the injector body 1. The operator will then twist the flange or sleeve clockwise or anticlockwise, relative to one another and around their longitudinal axis. As a result, the thin bridges 23 will be broken so as to separate the sleeve 22 from the base 21. Subsequently, the sleeve 22 can be moved along the cylinder 14 toward the forward end, i.e., the needle end, until the sleeve's lugs 24 snap in the groove 25 of the base at a position where the sleeve 22 wholly covers the needle 3. The sleeve in this position cannot move forwards or backwards, since its lugs bear against the forward wall of the groove 25 to prevent forward movement and the rear tapered portion of the base 21 provides a sufficiently high rearward wall of the groove to prevent rearward movement. The composite syringe will be thrown away after the protecting sleeve 22 has been moved to a stable position covering the needle 3.

As will now be apparent, the composite syringe provided herein is simpler in structure, easier to operate and much less expensive than the syringes of the prior art types. Further, medical personnel and doctors are positively protected from being accidently and erroneously pricked by the used needles when discarding the used syringes.

What is claimed is:

1. A composite syringe comprising:
   an injector body; and
   a cylindrical protector covering the injector body;
   said injector body comprising:
   a cylinder;
   tip means extending from the cylinder for holding a medical needle; and
   a skirt surrounding the tip and extending coaxially thereof;
   said cylindrical protector comprising:
   a sleeve;
   a base surrounding the tip and extending from said sleeve to contact the tip, said sleeve connected to said base;
   said sleeve having an end portion breakable from an end portion of said base so that said sleeve is separable from said base and slidable on the cylinder toward said tip means, the syringe further including:

a lockable member formed on an inner periphery of said sleeve; and a locking member formed on an outer periphery of said base, the locking member being engageable with the lockable member so that said sleeve is locked in a position to circumferentially enclose the medical needle.

2. A composite syringe as defined in claim 1, wherein said base is connected to said sleeve by at least one bridge element.

3. A composite syringe as defined in claim 1, wherein said base and said sleeve are integral with one another and formed of materials substantially immiscible with each other.

4. A composite syringe as defined in claim 1, wherein the lockable member is a plurality of lugs positioned on an inner periphery of an end portion of said sleeve, and the locking member is an annular groove formed on an outer periphery of said base.

5. A composite syringe as defined in claim 1, wherein the lockable member is an annular groove provided on an inner periphery of an end portion of said sleeve, and the locking member is a plurality of lugs positioned on an outer periphery of said base.

6. A composite syringe as defined in claim 2, wherein the lockable member is a plurality of lugs positioned on ah inner periphery of an end portion of said sleeve, and the locking member is an annular groove formed on an outer periphery of said base.

7. A composite syringe as defined in claim 3, wherein the lockable member is a plurality of lugs positioned on an inner periphery of an end portion of said sleeve, and the locking member is an annular groove formed on an outer periphery of said base.

8. A composite syringe as defined in claim 2, wherein the lockable member is an annular groove provided on an inner periphery of an end portion of said sleeve, and the locking member is a plurality of lugs positioned on an outer periphery of said base.

9. A composite syringe as defined in claim 3, wherein the lockable member is an annular groove provided on an inner periphery of an end portion of said sleeve, and the locking member is a plurality of lugs positioned on an outer periphery of said base.

10. A composite syringe as defined in claim 1, wherein said sleeve is extendible concentrically with the medical needle to a length which is greater than a predetermined length of the medical needle.

* * * * *